United States Patent
Lin

(10) Patent No.: US 11,213,632 B2
(45) Date of Patent: Jan. 4, 2022

(54) SAFETY SYRINGE AND SAFETY MECHANISM FOR USE IN THE SAME

(71) Applicant: SOL-MILLENNIUM MEDICAL HK LIMITED, Hong Kong (CN)

(72) Inventor: Zuoqian Lin, Zhejiang (CN)

(73) Assignee: SOL-MILLENNIUM MEDICAL HK LIMITED, Hong Kong (CN)

(*) Notice: Subject to any disclaimer, the term of this patent is extended or adjusted under 35 U.S.C. 154(b) by 329 days.

(21) Appl. No.: 16/342,585

(22) PCT Filed: Mar. 24, 2017

(86) PCT No.: PCT/CN2017/078104
§ 371 (c)(1),
(2) Date: Apr. 17, 2019

(87) PCT Pub. No.: WO2018/170893
PCT Pub. Date: Sep. 27, 2018

(65) Prior Publication Data
US 2019/0255259 A1    Aug. 22, 2019

(51) Int. Cl.
*A61M 5/32* (2006.01)

(52) U.S. Cl.
CPC ........ *A61M 5/3245* (2013.01); *A61M 5/3202* (2013.01); *A61M 5/3257* (2013.01); *A61M 2005/3247* (2013.01)

(58) Field of Classification Search
CPC .................... A61M 5/3257; A61M 2005/3247
See application file for complete search history.

(56) References Cited

U.S. PATENT DOCUMENTS 5,411,492 A * 5/1995 Sturman ............. A61M 5/3269
                                                              128/919
5,480,385 A    1/1996 Thorne et al.
(Continued)

FOREIGN PATENT DOCUMENTS

CN    1171745 A    1/1998
CN    1277874 A    12/2000
(Continued)

OTHER PUBLICATIONS

Translation of and original International Search Report and the original Written Opinion dated Sep. 15, 2017 in counterpart International Application No. PCT/CN2017/078104, 10 pp.

(Continued)

*Primary Examiner* — Theodore J Stigell
*Assistant Examiner* — Rachel T. Smith
(74) *Attorney, Agent, or Firm* — Shumaker & Sieffert, P.A.

(57) ABSTRACT

The present invention discloses a safety syringe and a safety mechanism for use in the safety syringe. In one example, the safety syringe comprises: a barrel having a proximal end, a distal end and a cavity being between the proximal end and the distal end and defining a longitudinal axis, a needle holder extending distally from the distal end; a plunger having a distal portion inserted inside the barrel from the proximal end of barrel and a proximal portion located outside the barrel; a needle having a proximal portion inserted into a needle passage of the needle holder from the distal side of the needle holder and a distal portion located outside the needle holder, the needle being hollow and in fluid communication with the cavity of the barrel; and a safety mechanism mounted at least partially around the needle holder; at an unactuated position of the safety mechanism, the distal portion of the needle is not covered by the (Continued)

safety mechanism; at an actuated position of the safety mechanism, at least distal tip end of the needle is covered by the safety mechanism to prevent accidental contact with the distal tip end of the needle. According to the present disclosure, it is feasible to, upon assembling the syringe, first duly mount the safety mechanism, and then mount the needle. As such, the needle needs to be calibrated only once, and furthermore, the safety mechanism, before being actuated, does not interfere with the needle.

20 Claims, 10 Drawing Sheets

(56) References Cited

U.S. PATENT DOCUMENTS

| | | | |
|---|---|---|---|
| 5,487,734 A | 1/1996 | Thorne et al. | |
| 5,542,927 A | 8/1996 | Thorne et al. | |
| 5,549,708 A | 8/1996 | Thorne et al. | |
| 5,616,135 A | 4/1997 | Thorne et al. | |
| 5,656,031 A | 8/1997 | Thorne et al. | |
| 5,672,161 A * | 9/1997 | Allen | A61M 5/3202 604/192 |
| 5,823,997 A | 10/1998 | Thorne et al. | |
| 5,836,917 A | 11/1998 | Thorne et al. | |
| 5,928,200 A | 7/1999 | Thorne et al. | |
| 5,980,488 A | 11/1999 | Thorne et al. | |
| 6,015,397 A * | 1/2000 | Elson | A61M 5/3275 604/192 |
| 6,024,727 A | 2/2000 | Thorne et al. | |
| 6,086,563 A | 7/2000 | Moulton et al. | |
| 8,845,585 B2 | 9/2014 | Wang et al. | |
| 2007/0073237 A1 | 3/2007 | Rodd | |
| 2017/0216534 A1 | 8/2017 | Kawabe et al. | |
| 2018/0318500 A1 | 11/2018 | Lin | |

FOREIGN PATENT DOCUMENTS

| | | |
|---|---|---|
| CN | 1803209 A | 7/2006 |
| CN | 103239775 A | 8/2013 |
| CN | 205041892 U | 2/2016 |
| CN | 106237454 A | 12/2016 |
| EP | 0693299 A2 | 1/1996 |
| EP | 2070559 A1 | 6/2009 |
| WO | 2016021323 A1 | 2/2016 |

OTHER PUBLICATIONS

Office Action from U.S. Appl. No. 15/580,461, dated Jan. 28, 2020, 13 pp.
Response to Office Action dated Jan. 28, 2020, from U.S. Appl. No. 15/580,461, filed Apr. 28, 2020, 9 pp.
Notice of Allowance from U.S. Appl. No. 15/580,461, dated May 20, 2020, 11 pp.
Extended Search Report from counterpart European Application No. 17901976.5, dated Sep. 9, 2020, 7 pp.

* cited by examiner

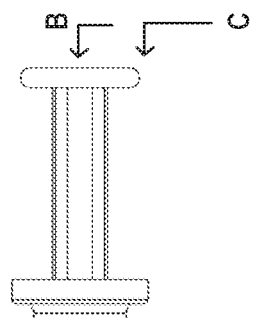
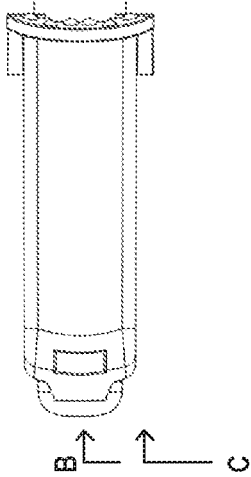
FIG.6

SAFETY SYRINGE AND SAFETY MECHANISM FOR USE IN THE SAME

This application is a U.S. national phase application under 37 U.S.C. § 371 of international application number PCT/CN2017/078104 filed on Mar. 24, 2017, the entire content of which is incorporated herein by reference.

TECHNICAL FIELD

The present invention relates to a safety syringe and a safety mechanism for use in the safety syringe.

BACKGROUND

A used syringe might accidentally pierce a person and cause infection of a disease. Therefore, the prior art teaches a syringe having an actuatable safety cover. The safety cover can be positioned to prevent accidental contact of a needle tip of the used syringe. In the prior art, the safety cover is provided with a blocking member for defending the needle tip, and the blocking member has a needle passage. During the assembling of the syringe, it is necessary to allow the needle to pass through the needle passage of the blocking member to mount the safety cover having the blocking member. At this time, since the needle might be touched during the mounting, the needle needs to be calibrated again, which is time-consuming and prone to cause errors.

SUMMARY

An object of the present disclosure is to solve the above problems existing in the prior art.

In an aspect, the present disclosure provides a safety syringe, comprising: a barrel having a proximal end, a distal end and a cavity being between the proximal end and the distal end and defining a longitudinal axis, a needle holder extending distally from the distal end; a plunger having a distal portion inserted inside the barrel from the proximal end of barrel and a proximal portion located outside the barrel; a needle having a proximal portion inserted into a needle passage of the needle holder from a distal side of the needle holder and a distal portion located outside the needle holder, the needle being hollow and in fluid communication with the cavity of the barrel; and a safety mechanism mounted at least partially around the needle holder; at an unactuated position of the safety mechanism, the distal portion of the needle is not covered by the safety mechanism; at an actuated position of the safety mechanism, at least distal tip end of the needle is covered by the safety mechanism to prevent accidental contact with the distal tip end of the needle.

In one example, the safety mechanism is axially snapped at least partially around the needle holder.

In one example, the safety mechanism is freely rotatable around the needle holder.

In one example, the safety mechanism comprises a guide locking member and a protective member, the guide locking member is mounted at least partially around the needle holder; the protective member is disposed at least partially around the needle holder and located at a distal side of the guide locking member, the protective member is movable from an unactuated position to an actuated position; at the unactuated position, the distal portion of the needle is not covered by the protective member; at the actuated position, at least distal tip end of the needle is covered by the protective member; the guide locking member and the protective member have a mechanism for releasably retaining the protective member at the unactuated position, a mechanism for guiding the protective member to move from the unactuated position to the actuated position, and a mechanism for locking the protective member at the actuated position.

In one example, the guide locking member comprises a sleeve portion mounted around the needle holder and a guide locking portion extending longitudinally and proximally from outside of the sleeve portion.

In one example, the protective member comprises a sleeve portion disposed around the needle holder at the distal side of the sleeve portion of the guide locking member, an arm portion extending longitudinally and proximally from the outside of the sleeve portion of the protective member, and a finger contact portion at a proximal end of the arm portion.

In one example, the mechanism for releasably retaining the protective member at the unactuated position comprises an elastic tab on the guide locking portion of the guide locking member and a bump longitudinally disposed on a side of the arm portion of the protective member facing towards the elastic tab; when at the unactuated position, at least a portion of the elastic tab on the guide locking portion is received at a distal side of the bump to retain the protective member at the unactuated position, the bump is shaped such that when a finger force towards the distal side is permitted to be applied to the finger contact portion of the protective member, the elastic tab on the guide locking portion passes over the bump to release the protective member from the unactuated position.

In one example, the mechanism for guiding the protective member to move from the unactuated position to the actuated position comprises at least one longitudinal guide slot on the guide locking portion of the guide locking member and at least one corresponding longitudinal flange on the arm portion of the protective member; when at the unactuated position, a distal portion of the longitudinal flange is located in the longitudinal guide slot, and the longitudinal guide slot and the longitudinal flange are shaped such that when a finger force towards the distal side is permitted to be applied to the finger contact portion of the protective member, the longitudinal flange slides distally along the longitudinal guide slot until the finger contact portion contacts the guide locking portion and stops.

In one example, the mechanism for locking the protective member at the actuated position comprises the elastic tab on the guide locking portion of the guide locking member and the bump longitudinally disposed on a side of the arm portion of the protective member towards the elastic tab, and at least one guide protrusion disposed at the proximal end of the protective member and at least one indentation disposed correspondingly on the guide locking portion of the locking member; when the protective member moves from the unactuated position to the actuated position, the elastic tab can pass over the bump and snap on the proximal side of the bump, and the guide protrusion is received in the indentation so that the protective member is locked at the actuated position in a manner of forming a slope with a longitudinal axis.

In one example, inside the sleeve portion of the guide locking member is provided a protrusion or indentation, and the protrusion or indentation engages an indentation or protrusion formed on the outside of the needle holder to axially snap the sleeve portion of the guide locking member on the barrel.

In one example, the safety syringe further comprises a needle cover which is used to cover the needle and shaped adapted for the shape of the safety mechanism.

Preferably, at least one pair of ribs are provided on an inner surface of the needle cover, and said at least one pair of ribs slidingly engage with at least one flange on the guide locking portion of the guide locking member.

In one example, the inner surface of the needle cover is further provided with a pair of ribs which are press-engaged with a wedge-shaped bump on the sleeve portion of the guide locking member.

In one example, a raised anti-slide bar is provided on an outer surface of the needle cover.

In one example, the sleeve portion of the protective member is formed as a cap with a top opening, and a bore diameter of the top opening is smaller than an inner diameter of a sleeve portion body of the protective member.

In one example, the finger contact portion is formed as a plate-shaped portion extending transversely from the proximal end of the arm portion of the protective member to the outside.

In another aspect, the present disclosure provides a safety mechanism for use in a safety syringe, the safety mechanism being mounted at least partially around a needle holder of the safety syringe; at an unactuated position of the safety mechanism, a distal portion of the needle is not covered by the safety mechanism; at an actuated position of the safety mechanism, at least distal tip end of the needle is covered by the safety mechanism to prevent accidental contact with the distal tip end of the needle.

In one example, the safety mechanism is axially snapped at least partially around the needle holder.

In one example, the safety mechanism is freely rotatable around the needle holder.

In one example, the safety mechanism comprises a guide locking member and a protective member, the guide locking member is mounted at least partially around the needle holder; the protective member is disposed at least partially around the needle holder and located at a distal side of the guide locking member, the protective member is movable from an unactuated position to an actuated position; at the unactuated position, the distal portion of the needle is not covered by the protective member; at the actuated position, at least distal tip end of the needle is covered by the protective member; the guide locking member and the protective member have a mechanism for releasably retaining the protective member at the unactuated position, a mechanism for guiding the protective member to move from the unactuated position to the actuated position, and a mechanism for locking the protective member at the actuated position.

In one example, the guide locking member comprises a sleeve portion mounted around the needle holder and a guide locking portion extending longitudinally and proximally from outside of the sleeve portion.

In one example, the protective member comprises a sleeve portion disposed around the needle holder at the distal side of the sleeve portion of the guide locking member, an arm portion extending longitudinally and proximally from the outside of the sleeve portion of the protective member, and a finger contact portion at a proximal end of the arm portion.

In one example, the mechanism for releasably retaining the protective member at the unactuated position comprises an elastic tab on the guide locking portion of the guide locking member and a bump longitudinally disposed on a side of the arm portion of the protective member facing towards the elastic tab; when at the unactuated position, at least a portion of the elastic tab on the guide locking portion is received at a distal side of the bump to retain the protective member at the unactuated position, the bump is shaped such that when a finger force towards the distal side is permitted to be applied to the finger contact portion of the protective member, the elastic tab on the guide locking portion passes over the bump to release the protective member from the unactuated position.

In one example, the mechanism for guiding the protective member to move from the unactuated position to the actuated position comprises at least one longitudinal guide slot on the guide locking portion of the guide locking member and at least one corresponding longitudinal flange on the arm portion of the protective member; when at the unactuated position, a distal portion of the longitudinal flange is located in the longitudinal guide slot, and the longitudinal guide slot and the longitudinal flange are shaped such that when a finger force towards the distal side is permitted to be applied to the finger contact portion of the protective member, the longitudinal flange slides distally along the longitudinal guide slot until the finger contact portion contacts the guide locking portion and stops.

In one example, the mechanism for locking the protective member at the actuated position comprises the elastic tab on the guide locking portion of the guide locking member and the bump longitudinally disposed on a side of the arm portion of the protective member facing towards the elastic tab, and at least one guide protrusion disposed at the proximal end of the protective member and at least one indentation disposed correspondingly on the guide locking portion of the locking member; when the protective member moves from the unactuated position to the actuated position, the elastic tab can pass over the bump and snap on the proximal side of the bump, and the guide protrusion is received in the indentation so that the protective member is locked at the actuated position in a manner of forming a slope with a longitudinal axis In one example, inside the sleeve portion of the guide locking member is provided a protrusion or indentation, and the protrusion or indentation engages an indentation or protrusion formed on the outside of the needle holder to axially snap the sleeve portion of the guide locking member on the barrel.

In one example, the sleeve portion of the protective member is formed as a cap with a top opening, and a bore diameter of the top opening is smaller than an inner diameter of a sleeve portion body of the protective member.

In one example, the finger contact portion is formed as a plate-shaped portion extending transversely from the proximal end of the arm portion of the protective member to the outside.

According to the present disclosure, since the safety mechanism is mounted on the needle holder of the barrel, it is feasible to, upon assembling the syringe, first duly mount the safety mechanism, and then mount the needle. As such, the needle needs to be calibrated only once, and furthermore, the safety mechanism, before being actuated, does not interfere with the needle.

According to the present disclosure, the safety mechanism is freely rotatable around the needle holder of the barrel so as to align a bevel of the needle tip.

According to the present disclosure, the safety mechanism follows a slope formed as the guide protrusion at the proximal end of the protective member is engaged with the indentation of the guide locking member, thereby achieving a purpose of deviating the needle tip to a side so that the needle tip is concealed in the protective cover.

In addition, as compared with the prior art, the safety syringe according to the present disclosure is structurally simple, smooth at the surface, operable with one hand and well protective for the needle, thereby preventing the needle from causing accidental injury.

BRIEF DESCRIPTION OF THE DRAWINGS

FIG. 6 is a side view of the safety syringe shown in FIG. 1, wherein the needle cover is removed and a safety mechanism is at an actuated position.

DETAILED DESCRIPTION

Reference is made to figures below to illustrate structures and working principles of the safety syringe, particularly its safety mechanism according to the present disclosure. However, those skilled in the art can readily envisage that the safety mechanism of the present disclosure is not limited to the syringe, and it may be applied to other medical instruments such as a blood collecting needle. "Proximal side", "distal side", "proximal end" and "distal end" mentioned in the text are all relative to the doctor who performs an injection operation. A side or end adjacent to the doctor who performs the injection operation is called "proximal side" and "proximal end", whereas a side or end away from the doctor who performs the injection operation is called "distal side" and "distal end".

Figure 1:
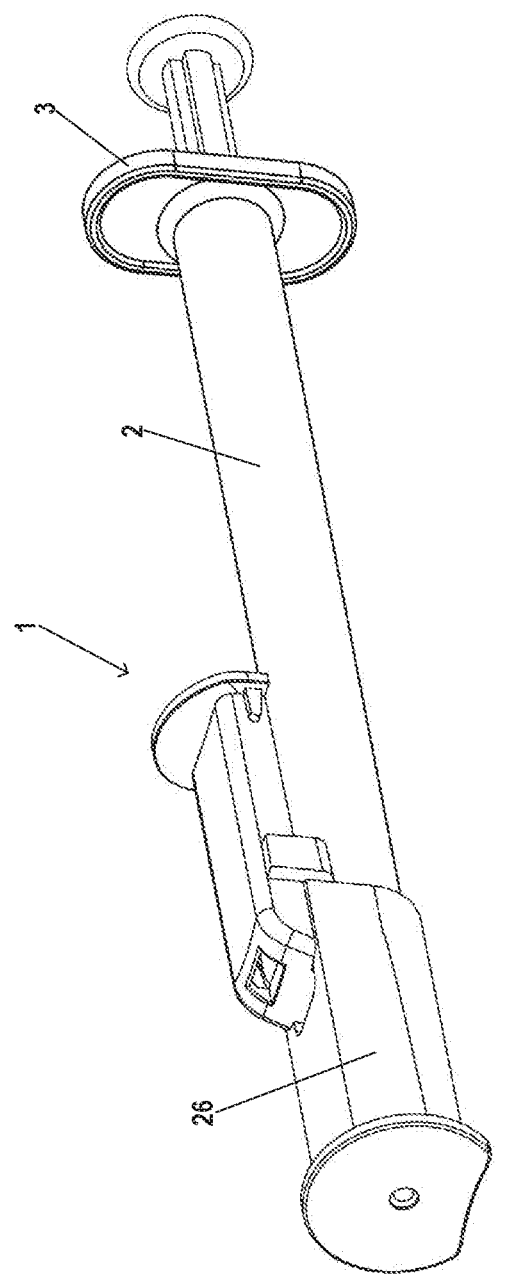
FIG. 1 is a perspective view of a safety syringe according to an embodiment of the present disclosure, wherein the safety syringe has a needle cover.

FIG. 1 is a perspective view of a safety syringe according to an embodiment of the present disclosure, wherein the safety syringe has a needle cover. The safety syringe 1 comprises a barrel 2, a plunger 7, a needle 8, a safety mechanism 9 and an optional needle cover 26. The barrel 2 has a proximal end 3, a distal end 4 and a cavity 5 being between the proximal end 3 and the distal end 4 and defining a longitudinal axis, and the cavity 5 is used to receive a medicament for injection. A needle holder 6 extends distally from the distal end 4 of the barrel 2, the needle holder 6 and the barrel 2 may be formed integrally or two parts connected together. The needle holder 6 has a central needle passage for receiving a portion of the needle and retaining the needle. The plunger 7 has a distal portion inserted inside the barrel 2 from the proximal end 3 of barrel and a proximal portion located outside the barrel. The needle 8 has a proximal portion inserted into the needle passage of the needle holder 6 from the distal side of the needle holder 6 and a distal portion located outside the needle holder 6, the needle is hollow, and it is inserted into the needle passage of the needle holder 6 and in fluid communication with the cavity 5 of the barrel 2. The safety mechanism 9 is mounted at least partially around the needle holder 6. At an unactuated position of the safety mechanism 9, the distal portion of the needle 8 is not covered by the safety mechanism 9. At an actuated position of the safety mechanism 9, at least distal tip end of the needle 8 is covered by the safety mechanism 9 to prevent accidental contact with the distal tip end of the needle 8. The safety mechanism 9 may be made of a thermoplastic material or any other suitable material. The optional needle cover 26 is used to cover the needle 8 and shaped adapted for the shape of the safety mechanism 9.

Figure 2:
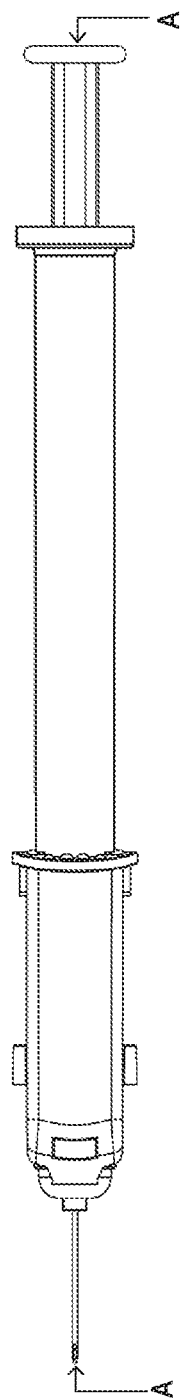
FIG. 2 is a side view of the safety syringe shown in FIG. 1, wherein the needle cover is removed and a safety mechanism is at an unactuated position.
Figure 3:
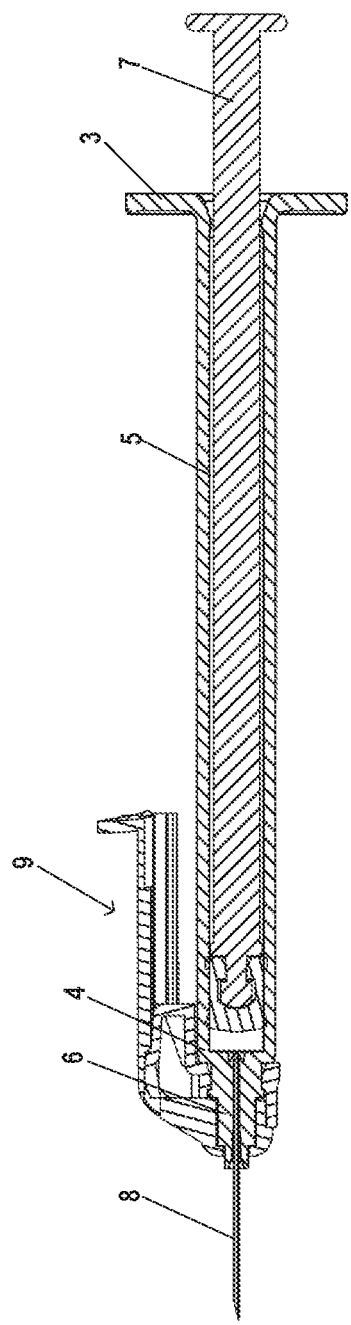
FIG. 3 is a sectional view taken along line A-A of FIG. 2.
Figure 4:
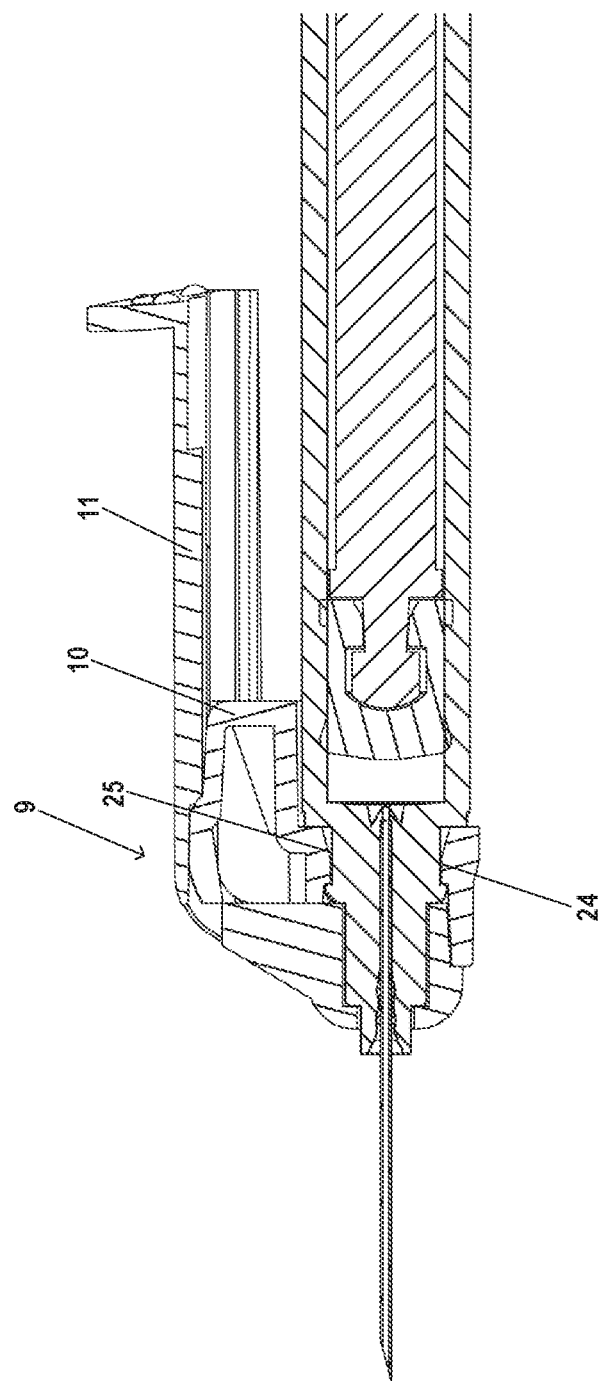
FIG. 4 is a partially enlarged view of FIG. 3
Figure 5:
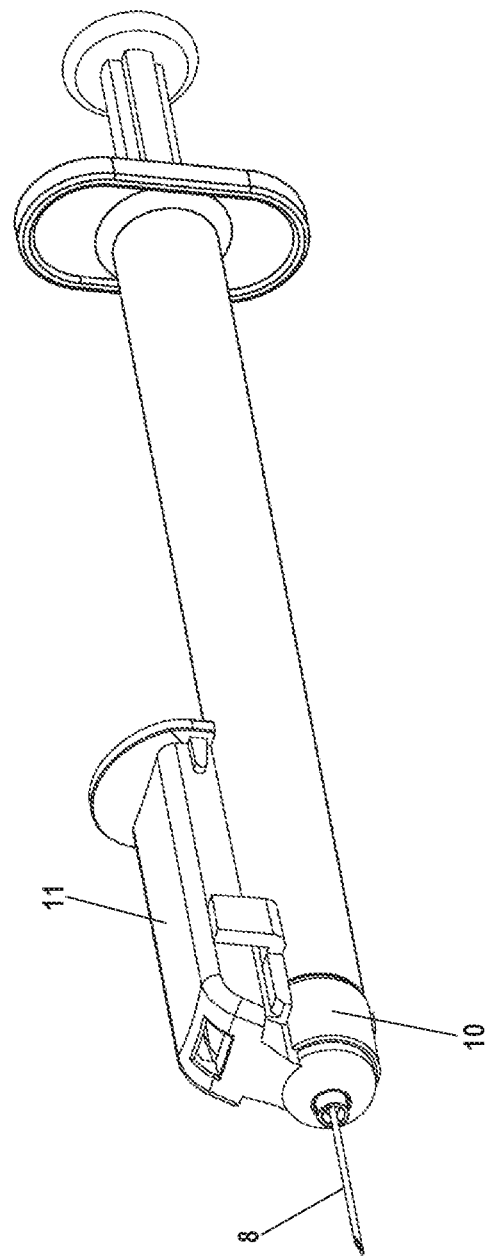
FIG. 5 is a perspective view of safety syringe shown in FIG. 1 when the needle cover is removed.

The safety mechanism 9 according to an embodiment of the present disclosure is described below in detail. FIG. 2 is a side view of the safety syringe shown in FIG. 1, wherein the needle cover is removed and the safety mechanism is at an unactuated position. FIG. 3 is a sectional view taken along line A-A of FIG. 2. FIG. 4 is a partially enlarged view of FIG. 3. Referring to FIG. 2 to FIG. 4, the safety mechanism 9 is axially snapped at least partially around the needle holder. In another embodiment, the safety mechanism 9 is freely rotatable around the needle holder to align a bevel of the needle tip. The safety mechanism 9 comprises a guide locking member 10 and a protective member 11. The guide locking member 10 comprises a sleeve portion 12 mounted around the needle holder 6 and a guide locking portion 13 extending longitudinally and proximally from outside of the sleeve portion 12.

A protrusion 24 may be disposed inside the sleeve portion 12 of the guide locking member 10. The protrusion 24 may engage with an indentation 25 formed on the outside of the needle holder 6 to axially snap the sleeve portion 12 of the guide locking member 10 on the barrel. On the contrary, an indentation may be disposed inside the sleeve portion 12 of the guide locking member 10, and the indentation may engage with a protrusion formed on the outside of the needle holder 6 to axially snap the sleeve portion 12 of the guide locking member 10 on the barrel. In the embodiment shown in FIG. 2 to FIG. 4, an outer diameter of the needle holder 6 is smaller than an inner diameter of the barrel 2 so that a retaining shoulder is formed at a boundary of the needle holder 6 and the barrel 2. A flange is disposed on the needle holder 6 at a longitudinal distance from the boundary position. Between the retaining shoulder and the flange is formed the indentation 25 for receiving the protrusion 24 inside the sleeve portion 12 of the guide locking member 10, to axially snap the sleeve portion 12 of the guide locking member 10 on the barrel.

Figure 7:
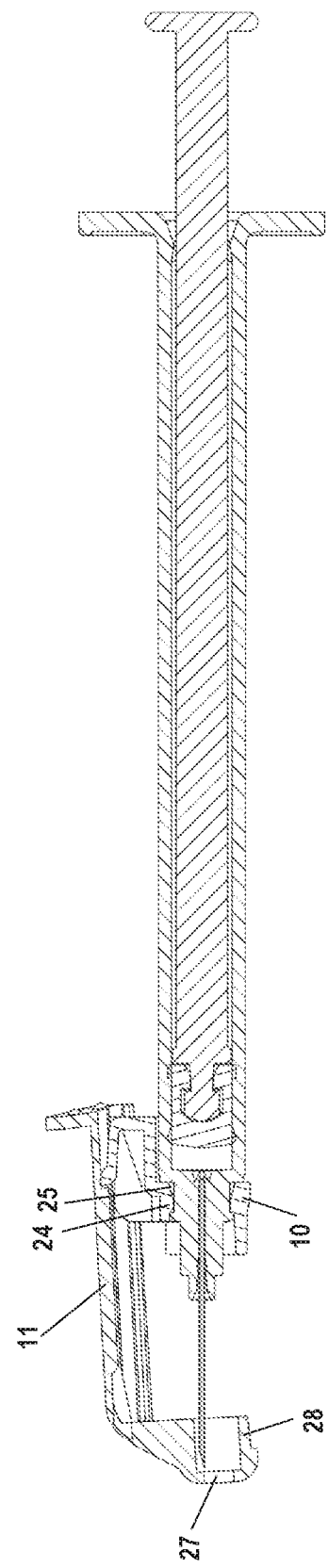
FIG. 7 is a sectional view taken along line B-B of FIG. 6.
Figure 10:
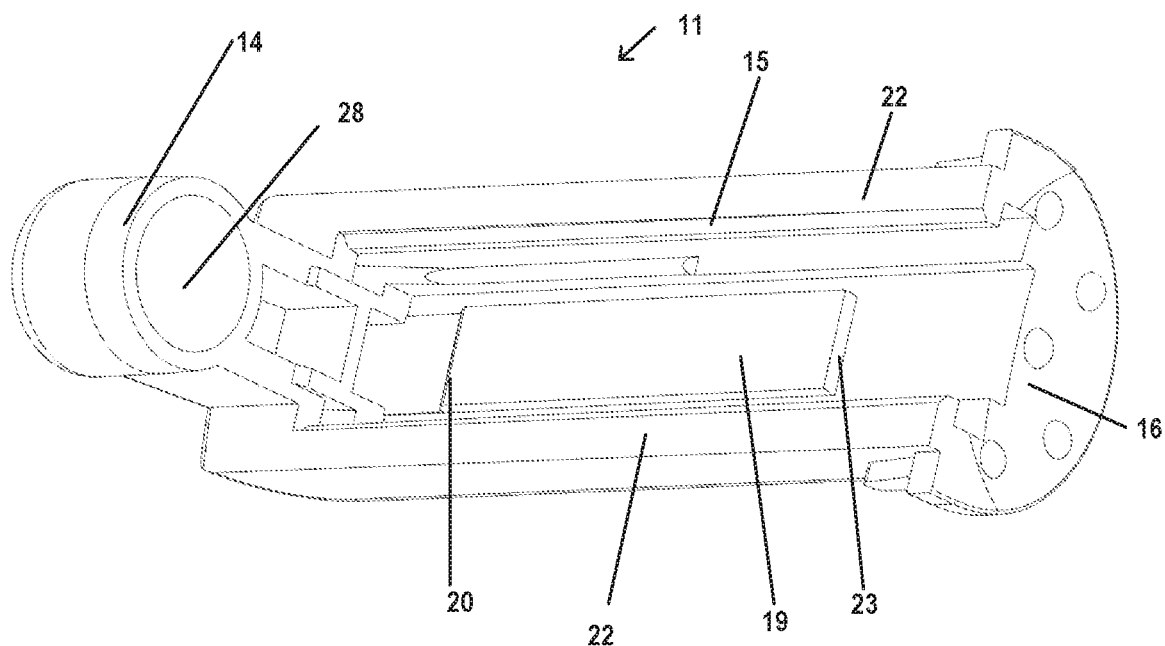
FIG. 10 is a perspective view of a protective member according to an embodiment of the present disclosure.

The protective member 11 may comprise a sleeve portion 14 around the needle holder 6 at the distal side of the sleeve portion 12 of the guide locking member 10, an arm portion 15 extending longitudinally proximally from the outside of the sleeve portion 14 of the protective member 11, and a finger contact portion 16 at the proximal end of the arm portion 15 (referring to FIG. 10). The finger contact portion 16 of the protective member 11 is preferably shaped as a plate-shaped portion extending transversely from the proximal end of the arm portion 15 of the protective member 11 to the outside. More preferably, a surface of the plate-shaped portion is provided with small protrusions to increase the touch feeling when the doctor pushes the protective member 11 with a finger. With a finger pressure being applied to the finger contact portion 16, the protective member 11 may move from an unactuated position (as shown in FIG. 3) to an actuated position (as shown in FIG. 7). When the protective member 11 is at the unactuated position, the distal portion of the needle 8 is not covered by the protective member 11; when the protective member 11 is at the actuated position, at least the distal tip end of the needle 8 is covered by the protective member 11.

The guide locking member 10 and the protective member 11 may have a mechanism for releasably retaining the protective member 11 at the unactuated position, a mechanism for guiding the protective member 11 to move from the unactuated position to the actuated position, and a mechanism for locking the protective member 11 at the actuated position.

Figure 9:
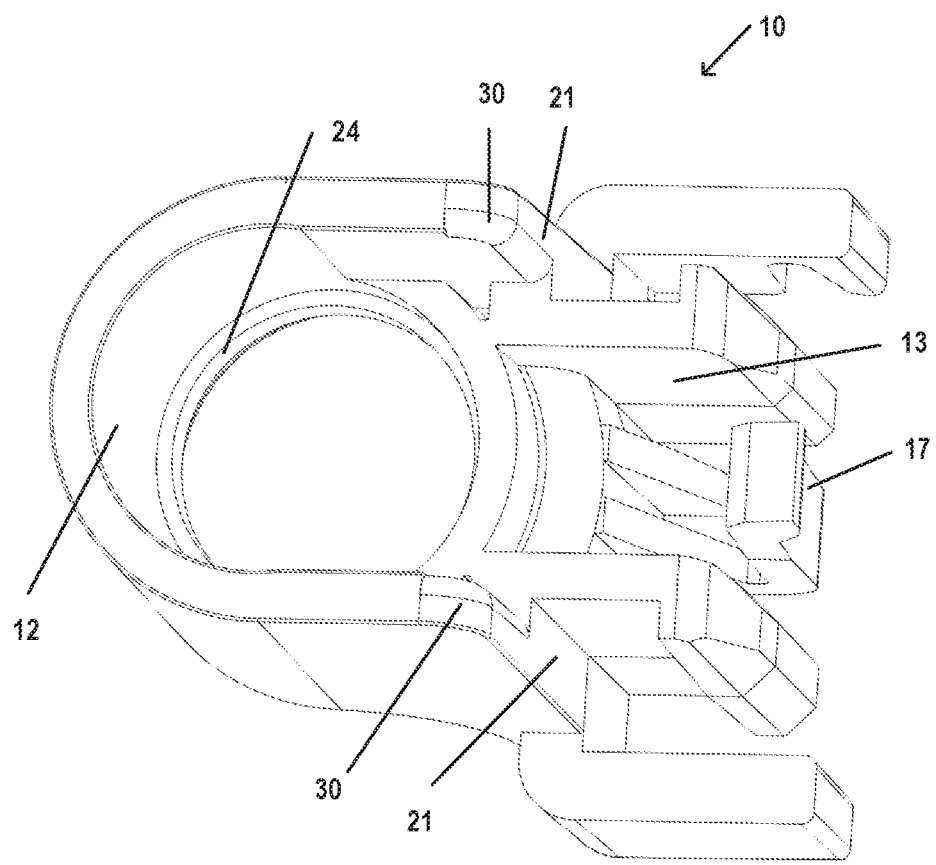
FIG. 9 is a perspective view of a guide locking member according to an embodiment of the present disclosure.

The mechanism for releasably retaining the protective member 11 at the unactuated position may comprise an elastic tab 17 on the guide locking portion 13 of the guide locking member 10 (referring to FIG. 9) and a bump 19 longitudinally disposed on a side of the arm portion 15 of the protective member 11 facing towards the elastic tab 17 (referring to FIG. 10). Preferably, the elastic tab 17 is a projecting tab extending angularly and distally from the guide locking portion 13, and the projecting tab is provided with a claw which can be snap fitted at a distal end 20 of the bump 19 on the arm portion 15 to retain the protective member at the unactuated position. According to another embodiment, a plurality of bumps 19 may be disposed longitudinally along the arm portion 15 of the protective member 11. The bumps 19 are shaped such that when a finger force towards the distal side is permitted to be applied to the finger contact portion of the protective member, the elastic tab 17 on the guide locking portion 13 passes over the bumps 19 to release the protective member from the unactuated position.

The mechanism for guiding the protective member 11 to move from the unactuated position to the actuated position comprises at least one longitudinal guide slot 21 on the guide locking portion 13 of the guide locking member 10 and at least one corresponding longitudinal flange 22 on the arm portion 15 of the protective member 11. Preferably, a longitudinal guide slot 21 is disposed on both left and right sides of the guide locking portion 13, and correspondingly, a longitudinal flange 22 is disposed at a position on the arm portion 15 of the protective member 11 corresponding to the longitudinal guide slot 21. At the unactuated position, a distal portion of the longitudinal flange 22 is located in the longitudinal guide slot 21, and the longitudinal guide slot 21 and the longitudinal flange 22 are shaped such that when a finger force towards the distal side is permitted to be applied to the finger contact portion 16 of the protective member 11, the longitudinal flange 22 slides distally along the longitudinal guide slot 21 until the finger contact portion 16 contacts the guide locking portion 13 and stops.

Figure 8:
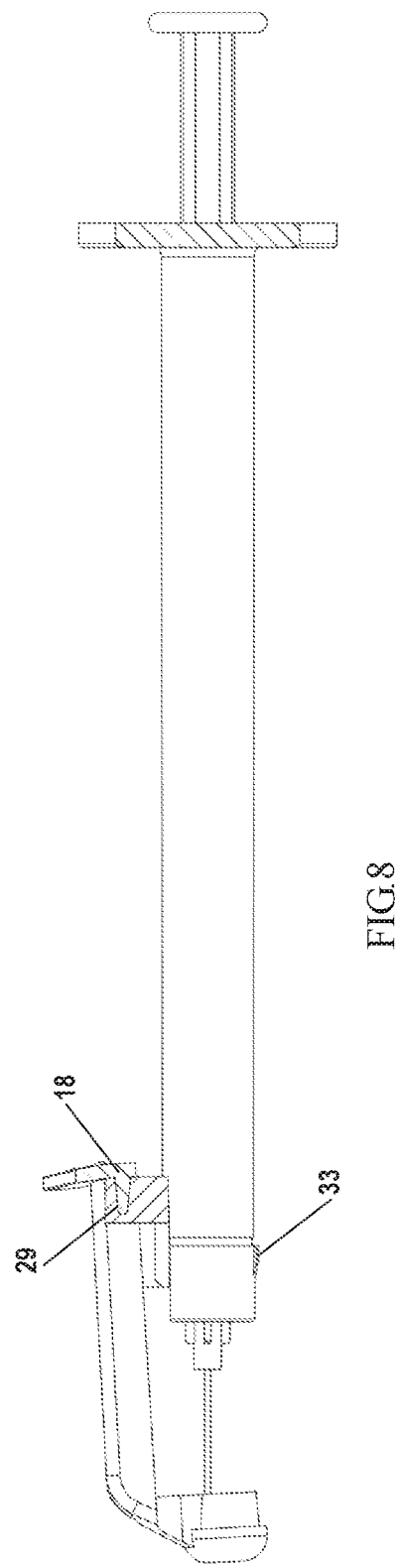
FIG. 8 is a sectional view taken along line C-C of FIG. 6.

The mechanism for locking the protective member 11 at the actuated position comprises the elastic tab 17 on the guide locking portion 13 of the guide locking member 10 and the bump 19 longitudinally disposed on a side of the arm portion 15 of the protective member 11 facing towards the tab 17, and at least one guide protrusion 18 disposed at the proximal end of the protective member and at least one indentation 29 disposed on the guide locking portion of the locking member. Preferably, a guide protrusion 18 is disposed on both left and right sides of the protective member, and correspondingly, an indentation 29 is disposed on both left and right sides of the proximal end of the guide locking portion of the locking member. Furthermore, preferably, the sleeve portion 14 of the protective member 11 is formed as a cap with a top opening 27. A bore diameter of the top opening 27 is smaller than an inner diameter of a sleeve portion body 28 of the protective member. When the protective member moves from the unactuated position to the actuated position, the elastic tab 17 can pass over the bump 19 and snaps on the proximal side 23 of the bump 19 (as shown in FIG. 7), and the guide protrusion 18 is received in the indentation 29 (as shown in FIG. 8) so that the longitudinal axis of the protective member 11 at the actuated position and a longitudinal axis of the syringe form an angle such that the needle does not align with the top opening 27 of the cap-like sleeve portion 14 of the protective member 11, but abuts against an inner wall of the sleeve portion body, further increasing safety of avoiding needle injury.

According to another embodiment of the present disclosure, the mechanism for releasably retaining the protective member at the unactuated position, the mechanism for guiding protective member to move from the unactuated position to the actuated position, and the mechanism for locking the protective member at the actuated position of the guide locking member 10 and the protective member 11 may comprise: a bump disposed longitudinally on the guide locking portion of the guide locking member and an elastic tab on a side of the arm portion of the protective member facing towards the elastic tab; at least one longitudinal flange on the guide locking portion of the guide locking member and at least one corresponding longitudinal slot on the arm portion of the protective member; and a bump longitudinally disposed on the guide locking portion of the guide locking member and an elastic tab on a side of the arm portion of the protective member facing towards the bump and at least one indentation disposed at the proximal end of the protective member and at least one protrusion disposed correspondingly on the guide locking portion of the locking member, so long as that the protective member moves from the unactuated position to the actuated position.

Figure 11:
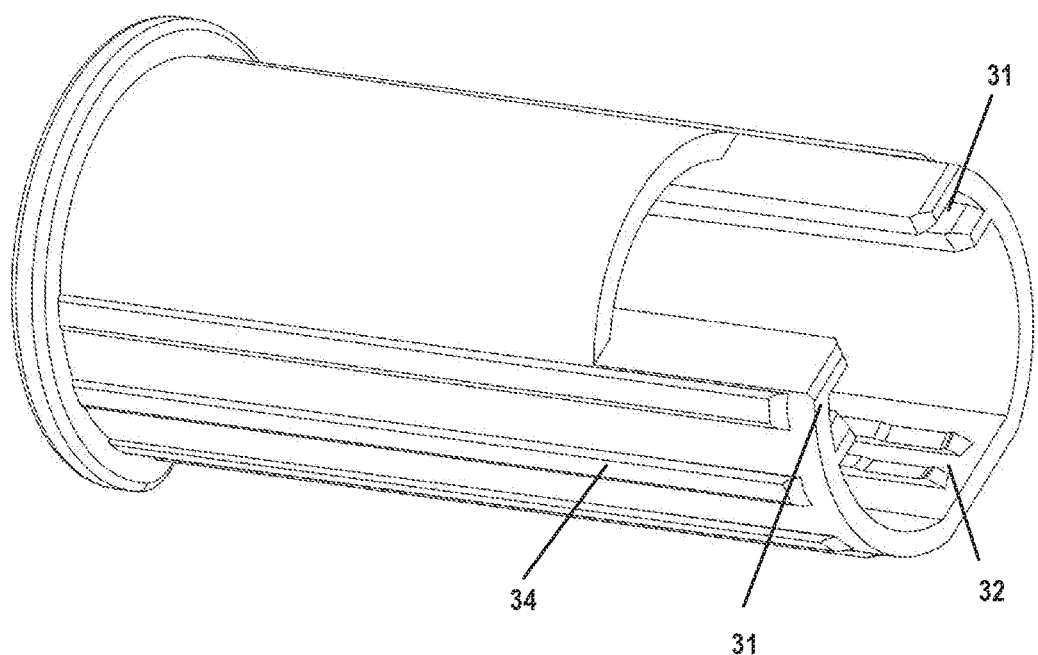
FIG. 11 is a perspective view of a needle cover according to an embodiment of the present disclosure.
Figure 12:
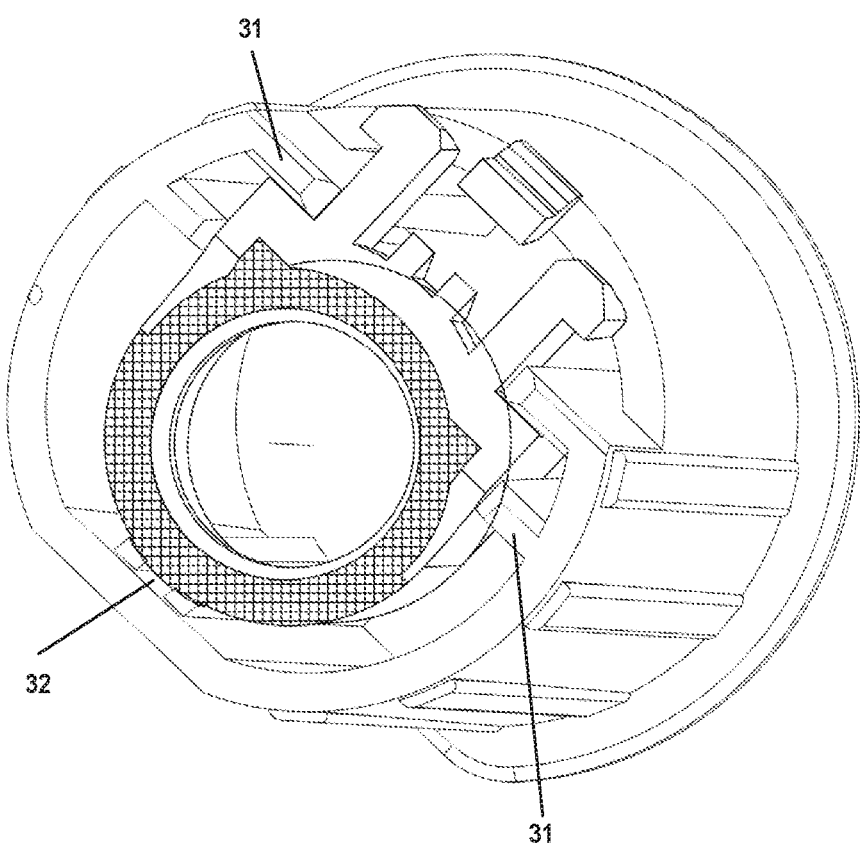
FIG. 12 is a perspective view in which the needle cover of FIG. 11 engages the guide locking member.

FIG. 11 is a perspective view of a needle cover 26 according to an embodiment of the present disclosure. As shown in the figure, an inner surface of the needle cover 26 is provided with a pair of ribs 31 at both sides of a notch portion, and each pair of ribs 31 respectively engage with a flange 30 on the guide locking portion 13 of the guide locking member. In addition, the inner surface of the needle cover 26 is further provided with a pair of ribs 32. Preferably, the pair of ribs 32 are circumferentially located at a substantially middle position of the two pairs of rib 31, and engage with a wedge-shaped bump 33 on the sleeve portion 12 of the guide locking member. When the protective member 11 is at the unactuated position, the needle cover 26 moves from the distal side of the needle 8 to the proximal side and covers the needle 8. During the movement, the ribs 31 on the inner surface of the needle cover 26 slidingly engage with the flange 30 on the guide locking portion 13 of the guide locking member, and ribs 32 on the inner surface of the needle cover 26 are press-engaged with the wedge-shaped bump 33 on the sleeve portion 12 of the guide locking member, to firmly fix the needle cover 26 (referring to FIG. 12). In addition, the outer surface of the needle cover 26 is provided with a raised anti-slide bar 34 to facilitate removal of the needle cover 26 upon use.

Specific structures of the present disclosure are described with reference to specific embodiments shown in figures. However, those skilled in the art should appreciate that the above detailed depictions are exemplary. Those skilled in the art, according to the above depictions, can make variations and improvements without departing from the scope of the present disclosure.

What is claimed is:

1. A safety syringe, comprising:
a barrel having a proximal end, a distal end and a cavity being between the proximal end and the distal end and defining a longitudinal axis, a needle holder extending distally from the distal end;
a plunger having a distal portion inserted inside the barrel from the proximal end of the barrel and a proximal portion located outside the barrel;
a needle having a proximal portion inserted into a needle passage of the needle holder from a distal side of the needle holder and a distal portion located outside the needle holder, the needle being hollow and in fluid communication with the cavity of the barrel; and
a safety mechanism mounted at least partially around the needle holder,
wherein at an unactuated position of the safety mechanism, the distal portion of the needle is not covered by the safety mechanism, and
wherein at an actuated position of the safety mechanism, at least a distal tip end of the needle is covered by the safety mechanism to prevent accidental contact with the distal tip end of the needle,
wherein the safety mechanism comprises a guide locking member and a protective member, the guide locking member being mounted at least partially around the needle holder;
wherein the protective member is disposed at least partially around the needle holder and located at a distal side of the guide locking member, and the protective member is movable from the unactuated position to the actuated position,
wherein at the unactuated position, the distal portion of the needle is not covered by the protective member,
wherein at the actuated position, at least the distal tip end of the needle is covered by the protective member,
wherein the guide locking member and the protective member have a mechanism for releasably retaining the protective member at the unactuated position, a mechanism for guiding the protective member to move from the unactuated position to the actuated position, and a mechanism for locking the protective member at the actuated position,
wherein the guide locking member comprises a sleeve portion mounted around the needle holder and a guide locking portion extending longitudinally and proximally from an outside of the sleeve portion,
wherein the protective member comprises a sleeve portion disposed around the needle holder at a distal side of the sleeve portion of the guide locking member, an arm portion extending longitudinally and proximally from the outside of the sleeve portion of the protective member, and a finger contact portion at a proximal end of the arm portion,
wherein the mechanism for releasably retaining the protective member at the unactuated position comprises an elastic tab on the guide locking portion of the guide locking member and a bump longitudinally disposed on a side of the arm portion of the protective member facing towards the elastic tab, and
wherein, when at the unactuated position, at least a portion of the elastic tab on the guide locking portion is received at a distal side of the bump to retain the protective member at the unactuated position, and the bump is shaped such that when a finger force towards the distal side of the bump is permitted to be applied to the finger contact portion of the protective member, the elastic tab on the guide locking portion passes over the bump to release the protective member from the unactuated position.

2. The safety syringe according to claim 1, wherein the safety mechanism is axially snapped at least partially around the needle holder.

3. The safety syringe according to claim 1, wherein the safety mechanism is freely rotatable around the needle holder.

4. The safety syringe according to claim 1,
wherein the mechanism for guiding the protective member to move from the unactuated position to the actuated position comprises at least one longitudinal guide slot on the guide locking portion of the guide locking member and at least one corresponding longitudinal flange on the arm portion of the protective member; and
wherein, when at the unactuated position, a distal portion of the at least one longitudinal flange is located in the at least one longitudinal guide slot, and the longitudinal guide slot and the at least one longitudinal flange are shaped such that when the finger force towards the distal side of the bump is permitted to be applied to the finger contact portion of the protective member, the at least one longitudinal flange slides distally along the at least one longitudinal guide slot until the finger contact portion contacts the guide locking portion and stops.

5. The safety syringe according to claim 4,
wherein the mechanism for locking the protective member at the actuated position comprises the elastic tab on the guide locking portion of the guide locking member and the bump longitudinally disposed on the side of the arm portion of the protective member towards the elastic tab, and at least one guide protrusion disposed at the proximal end of the protective member, and at least one indentation disposed correspondingly on the guide locking portion of the locking member; and
wherein when the protective member moves from the unactuated position to the actuated position, the elastic tab passes over the bump and snap on the proximal side of the bump, and the guide protrusion is received in the at least one indentation so that the protective member is locked at the actuated position in a manner of forming a slope with the longitudinal axis.

6. The safety syringe according to claim 1, wherein inside the sleeve portion of the guide locking member is provided a protrusion or indentation, and the protrusion or indentation engages an indentation or protrusion formed on the outside of the needle holder to axially snap the sleeve portion of the guide locking member on the barrel.

7. The safety syringe according to claim 1, wherein the safety syringe further comprises a needle cover which is used to cover the needle and shaped adapted for the shape of the safety mechanism.

8. The safety syringe according to claim 7, wherein at least one pair of ribs are provided on an inner surface of the needle cover, and said at least one pair of ribs slidingly engage with at least one flange on the guide locking portion of the guide locking member.

9. The safety syringe according to claim 8, wherein the inner surface of the needle cover is further provided with a pair of ribs which are press-engaged with a wedge-shaped bump on the sleeve portion of the guide locking member.

10. The safety syringe according to claim 9, wherein a raised anti-slide bar is provided on an outer surface of the needle cover.

11. The safety syringe according to claim 1, wherein the sleeve portion of the protective member is formed as a cap with a top opening, and a bore diameter of the top opening is smaller than an inner diameter of a sleeve portion body of the protective member.

12. The safety syringe according to claim 1, wherein the finger contact portion is formed as a plate-shaped portion extending transversely from the proximal end of the arm portion of the protective member to the outside.

13. A safety mechanism for use in a safety syringe, the safety mechanism being mounted at least partially around a needle holder of the safety syringe;
   wherein at an unactuated position of the safety mechanism, a distal portion of a needle is not covered by the safety mechanism; and
   wherein at an actuated position of the safety mechanism, at least a distal tip end of the needle is covered by the safety mechanism to prevent accidental contact with the distal tip end of the needle,
   wherein the safety mechanism comprises a guide locking member and a protective member, the guide locking member being mounted at least partially around the needle holder;
   wherein the protective member is disposed at least partially around the needle holder and located at a distal side of the guide locking member, the protective member being movable from the unactuated position to the actuated position,
   wherein at the unactuated position, the distal portion of the needle is not covered by the protective member,
   wherein at the actuated position, at least the distal tip end of the needle is covered by the protective member, and
   wherein the guide locking member and the protective member have a mechanism for releasably retaining the protective member at the unactuated position, a mechanism for guiding the protective member to move from the unactuated position to the actuated position, and a mechanism for locking the protective member at the actuated position,
   wherein the guide locking member comprises a sleeve portion mounted around the needle holder and a guide locking portion extending longitudinally and proximally from an outside of the sleeve portion,
   wherein the protective member comprises a sleeve portion disposed around the needle holder at a distal side of the sleeve portion of the guide locking member, an arm portion extending longitudinally and proximally from the outside of the sleeve portion of the protective member, and a finger contact portion at a proximal end of the arm portion,
   wherein the mechanism for releasably retaining the protective member at the unactuated position comprises an elastic tab on the guide locking portion of the guide locking member and a bump longitudinally disposed on a side of the arm portion of the protective member facing towards the elastic tab, and
   wherein, when at the unactuated position, at least a portion of the elastic tab on the guide locking portion is received at a distal side of the bump to retain the protective member at the unactuated position, and the bump is shaped such that when a finger force towards the distal side of the bump is permitted to be applied to the finger contact portion of the protective member, the elastic tab on the guide locking portion passes over the bump to release the protective member from the unactuated position.

14. The safety mechanism according to claim 13, wherein the safety mechanism is axially snapped at least partially around the needle holder.

15. The safety mechanism according to claim 13, wherein the safety mechanism is freely rotatable around the needle holder.

16. The safety mechanism according to claim 13,
   wherein the mechanism for guiding the protective member to move from the unactuated position to the actuated position comprises at least one longitudinal guide slot on the guide locking portion of the guide locking member and at least one corresponding longitudinal flange on the arm portion of the protective member; and
   wherein, when at the unactuated position, a distal portion of the at least one longitudinal flange is located in the at least one longitudinal guide slot, and the longitudinal guide slot and the at least one longitudinal flange are shaped such that when the finger force towards the distal side of the bump is permitted to be applied to the finger contact portion of the protective member, the at least one longitudinal flange slides distally along the at least one longitudinal guide slot until the finger contact portion contacts the guide locking portion and stops.

17. The safety mechanism according to claim 16,
   wherein the mechanism for locking the protective member at the actuated position comprises the elastic tab on the guide locking portion of the guide locking member and the bump longitudinally disposed on the side of the arm portion of the protective member facing towards the elastic tab), and at least one guide protrusion disposed at the proximal end of the protective member and at least one indentation disposed correspondingly on the guide locking portion of the locking member; and
   wherein, when the protective member moves from the unactuated position to the actuated position, the elastic tab can pass over the bump and snap on the proximal side of the bump, and the guide protrusion is received in the indentation so that the protective member is locked at the actuated position in a manner of forming a slope with the longitudinal axis.

18. The safety mechanism according to claim 13, wherein inside the sleeve portion of the guide locking member is provided a protrusion or indentation, and the protrusion or indentation engages an indentation or protrusion formed on the outside of the needle holder to axially snap the sleeve portion of the guide locking member on the barrel.

19. The safety mechanism according to claim 13, wherein the sleeve portion of the protective member is formed as a cap with a top opening, and a bore diameter of the top opening is smaller than an inner diameter of a sleeve portion body of the protective member.

20. The safety mechanism according to claim 13, wherein the finger contact portion is formed as a plate-shaped portion extending transversely from the proximal end of the arm portion of the protective member to the outside.

\* \* \* \* \*